United States Patent
Bergeron et al.

(10) Patent No.: US 6,880,701 B2
(45) Date of Patent: *Apr. 19, 2005

(54) STORAGE CONTAINER FOR AT LEAST ONE HYPODERMIC NEEDLE

(75) Inventors: Luc Bergeron, Boussens (CH);
Grégoire Bosset, Preverenges (CH);
Jérôme Moulin, St-Maurice (CH);
Laurent Soldini, Lausanne (CH)

(73) Assignee: Ares Trading S.A., Aubonne (CH)

( * ) Notice: Subject to any disclaimer, the term of this patent is extended or adjusted under 35 U.S.C. 154(b) by 181 days.

This patent is subject to a terminal disclaimer.

(21) Appl. No.: 10/289,854

(22) Filed: Nov. 7, 2002

(65) Prior Publication Data

US 2003/0121815 A1 Jul. 3, 2003

Related U.S. Application Data

(63) Continuation of application No. PCT/IB01/00827, filed on May 15, 2001.

(30) Foreign Application Priority Data

May 15, 2000 (EP) .............................. 00810415

(51) Int. Cl.$^7$ ........................... B65D 83/10; A61B 5/00; A61M 5/32
(52) U.S. Cl. ..................... 206/365; 206/366; 600/576; 600/577; 604/192
(58) Field of Search ............................... 206/365–366; 220/908; 604/110, 192, 263; 600/576, 577; 29/240

(56) References Cited

U.S. PATENT DOCUMENTS

| | | | | |
|---|---|---|---|---|
| 4,932,418 A | * | 6/1990 | Coburn | 600/577 |
| 4,989,307 A | * | 2/1991 | Sharpe et al. | 29/240 |
| 5,038,929 A | * | 8/1991 | Kubofcik | 206/210 |
| 5,092,462 A | * | 3/1992 | Sagstetter et al. | 206/366 |
| 5,273,161 A | * | 12/1993 | Sagstetter | 206/366 |
| 5,347,078 A | | 9/1994 | Eckels | |
| 5,409,112 A | * | 4/1995 | Sagstetter | 206/366 |
| 5,545,145 A | * | 8/1996 | Clinton et al. | 604/192 |
| 5,810,167 A | * | 9/1998 | Fujii | 206/365 |
| 5,968,021 A | | 10/1999 | Ejlersen | |

FOREIGN PATENT DOCUMENTS

| | | |
|---|---|---|
| DE | 3903974 | 8/1990 |
| FR | 2 665 079 | 7/1990 |
| WO | WO 92/13585 | 8/1992 |
| WO | WO 97/40869 | 11/1997 |

* cited by examiner

Primary Examiner—Bryon P. Gehman
(74) Attorney, Agent, or Firm—Sturm & Fix LLP

(57) ABSTRACT

The connecting end of this storage container for at least one hypodermic needle has connectors complementary to the connectors on the tip of an injection instrument, one of the connectors having radial elasticity and devices for converting an axial force exerted between the needle and the injection instrument into at least one radial component which can deform the elastic connectors. The container has a housing fore the needle designed to hold this needle in a given position and an opening giving access to the housing. The shape and dimensions of the exterior wall bounding the housing are selected to create with the needle an ergonomic positioning and/or handling interface so as to facilitate the connection of the complementary connectors of the needle and the tip, respectively.

11 Claims, 4 Drawing Sheets

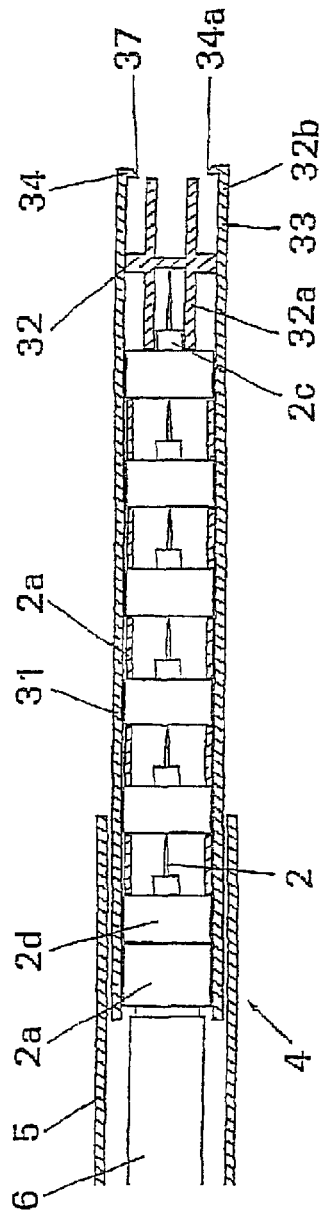
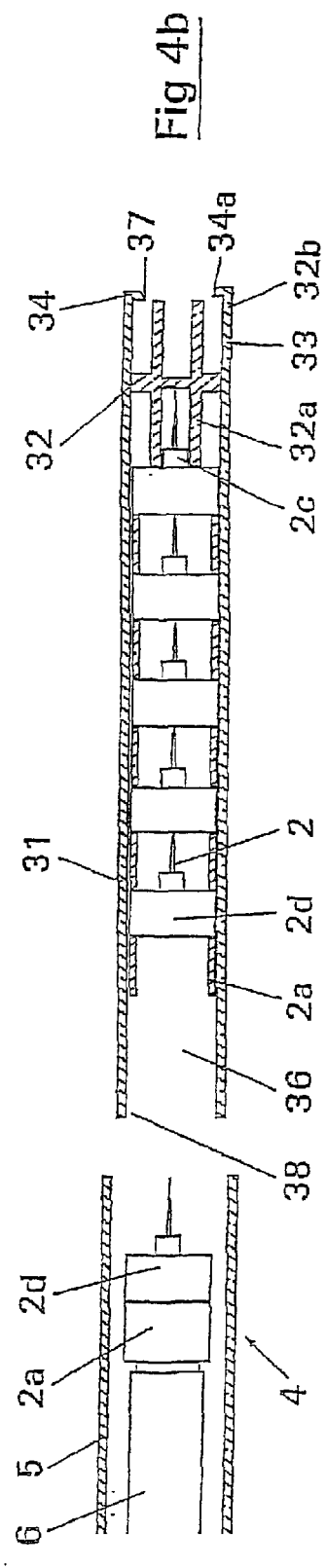
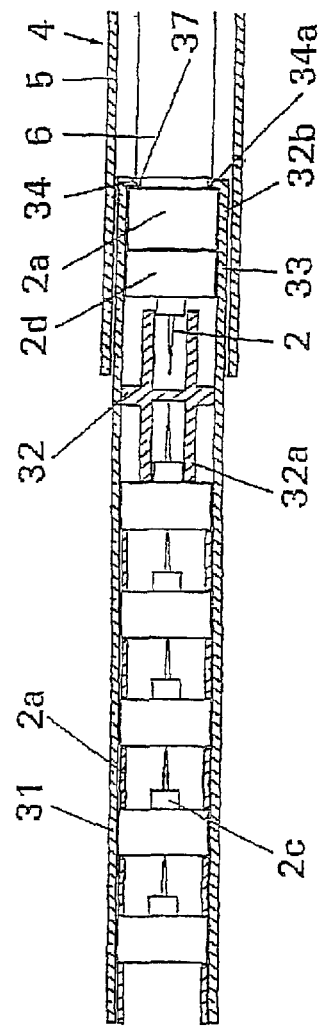

STORAGE CONTAINER FOR AT LEAST ONE HYPODERMIC NEEDLE

This Application is a continuation of PCT/IB01/00827 filed May 15, 20001.

TECHNICAL FIELD OF THE INVENTION

The invention relates to a container for storing, handling and disposing of injection needles.

BACKGROUND OF THE INVENTION

The invention relates to a storage container for at least one hypodermic needle. The connecting end of the needle has connectors which are complementary to connectors on the tip of an injection instrument, one of the connectors having radial elasticity and means for converting an axial force exerted between the needle and the injection instrument into at least one radial component capable of deforming the elastic connectors, and with a housing designed to hold the hypodermic needle in a determinate position and an opening affording access to the housing.

Hypodermic needles of this type are found on the market. Fixing them to the tip of an injection instrument is easier and faster because it is no longer necessary to screw in the needle, mere pressure along the axis sufficing to make the complementary connectors engage. Theoretically it should also be possible to separate them by traction along the axis, but the absence of purchase makes this operation difficult and it is performed in the traditional manner, by unscrewing.

In the case of chronic disorders, the patient may perform the injection himself. It is therefore important that the means of storing, handling and disposing of injection needles be not only safe, but relatively foolproof and easy to understand and manipulate.

U.S. Pat. No. 5,968,021 (Oct. 19, 1999) describes a magazine for storing injection needles. The user inserts an injection instrument in a predetermined radial orientation to the magazine. The needle can be released from the injection instrument by applying pressure at predetermined radial locations on the magazine.

International publication WO 92/13585 (Aug. 20, 1992) describes a needle container comprising a conical housing. Prior to use, the needle is held by frictional forces at the open end of the conical housing. After use of the needle, the user can re-insert the needle into the conical housing, pushing the needle below elastic tabs at the open end of the conical housing. The resilient tabs snap back after the needle is fully inserted, preventing the needle from being withdrawn.

In all of the prior art cases, when the neddle is fixed at the outlet end of the syringe, the user is no longer protected from injury by the needle. Several injection devices have been proposed to obviate this inconvenience and comprise to this end a mechanism for effecting the injection, which is movable by a cocking means counter to the force of a spring into a cocking position, from which it can be released to effect an injection process, so as to act upon a piston containing fluid to be injected.

A device of this type is disclosed for example in EP 0 359 761. The housing of this device is approximately the shape of an oversize fountain pen, and the injection needle is inside the device as long as an injection process has not to be effected. The injection device has a mechanism used to effect the injection process, which mechanism can be moved by means of a cocking element counter to the force of a spring into a cocked position from which it can be released in order to effect an injection process. This mechanism moves axially the hypodermic needle in order it protrudes from the forward end of the housing of the device which is put into contact whith the skin of the patient so that it is inserted through the skin and the liquid is injected.

With such a device, the means for connecting the needle to the injection device is inside the housing so that the user cannot see the precise position of the needle to be connected to the injection device, since it is hidden from sight by the housing of the injection device.

There remains a need for a safe and simple system for needle storage, handling and disposal, in particular for injection devices of the above-mentionned type.

SUMMARY OF THE INVENTION

It is an object of the invention to provide an easy-to-use and safe method for handling, storing and disposing of injection needles.

In a first aspect, the invention provides a storage container for at least one hypodermic needle, the hypodermic needle having a connecting end which has connectors complementary with connectors on the tip of an injection instrument, one of the connectors having radial elasticity and devices for converting an axial force exerted between the needle and the injection instrument into at least one radial component capable of deforming the elastic connectors, having a housing for the needle, designed so as to hold this needle in a determined position, and an opening giving access to the housing, characterized in that the exterior wall bounding the housing has guides coaxial with the longitudinal axis of the needle positioned in the housing and designed to engage with a complementary surface of the instrument so that, once these guides are engaged with each other the complementary connectors are in the assembling position, following the exertion of the axial pressure on the instrument. The presence of an ergonomic interface between the hypodermic needle and the user makes the handling and therefore the attachment of this needle easier and places the operation within the reach of a larger number of people.

DETAILED DESCRIPTION OF THE INVENTION

Advantageously, this container also has devices for facilitating the separation of a used needle from the injection instrument and for stocking it, so that the user may, given the same ergonomic support, connect and remove the needles much more simply and easily than in the case of needles supplied in bulk.

It is preferable that used needles which have been detached from the injection instrument stay trapped by the needle stand and are therefore no longer accessible, so that the used needles can be safely disposed of.

Other special features and advantages of the invention will become apparent from the following description, which is supported by the attached drawings illustrating, schematically and by way of example, one embodiment and variations of the container to which the present invention refers.

FIGS. 4a, 4b, 4c are sections of a third variation, showing three successive stages in the use of a hypodermic needle.

Figures 1A, 1B:
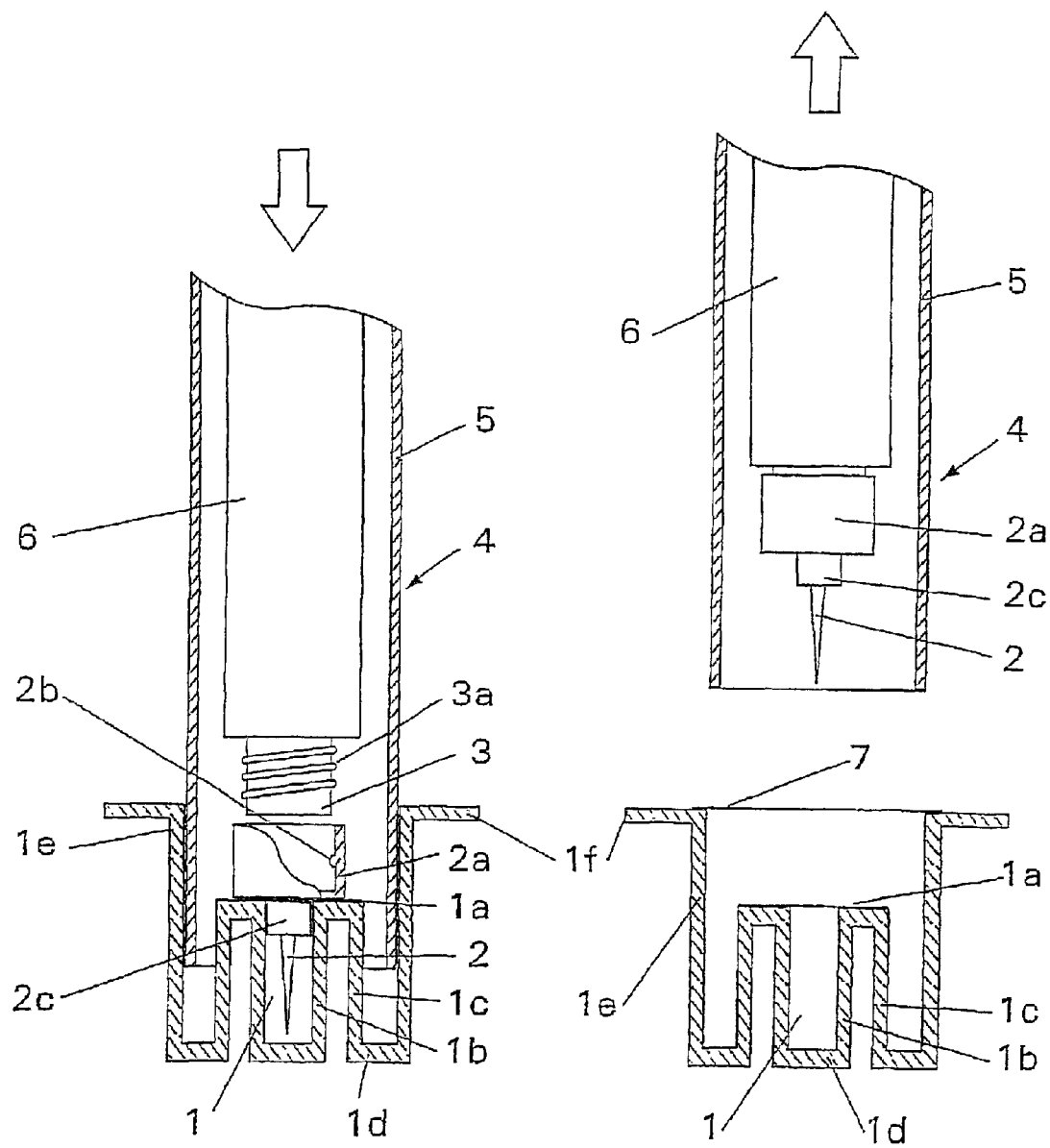
FIG. 1a is a vertical section of a first embodiment seen during the connection of a hypodermic needle to an injection instrument.
FIG. 1b is a section similar to FIG. 1a shown after the needle has been connected.

The storage container which is illustrated by FIGS. 1a and 1b has a housing delimited by a cylindrical wall 1 for receiving a hypodermic needle 2 forming one piece with a connecting end in the form of a hollow socket 2a whose inner face has a connector formed of at least one rib 2b. The hollow socket 2a is preferably made from an elastically deformable material so that it can dilate elastically and thereby allow the rib 2b to engage with a complementary connector, for example a rib, a groove or a thread 3a located on the outer face of a tip 3 of an injection instrument 4. As FIG. 1 shows the profile of the rib 2b allows a pressure along the axis to be converted into a radial component capable of elastically deforming the socket 2a.

In the embodiment illustrated here the injection instrument 4 resembles a ball-point pen in that it has a cylindrical barrel 5 accommodating a cartridge 6 which is intended to hold a dose of medicinal substance to be injected and whose forward end terminates in the connecting tip 3 intended to be pushed into the socket 2a of the hypodermic needle 2. This injection instrument 4 is of a known type, such as those disclosed e.g. in U.S. Pat. No. 5,092,842, in U.S. Pat. No. 5,114,406 or in EP 0 359 761, in which the hypodermic needle is retractable inside the cylindrical barrel in its rest position. Since this instrument is not part of the present invention, the rest of its structure and operation will not be described in greater detail.

The diameter of the cylindrical wall 1b of the housing 1 for the hypodermic needle 2 is calculated so as to allow the adjustment of an intermediate portion 2c located between the socket 2a and the needle properly so called, in order to position the needle 2 correctly. The upper lip 1a of the cylindrical wall 1b serves as a stop to a length of travel provided between the socket 2a and the intermediate portion 2c of the needle 2. A second cylindrical wall 1c, coaxial with the cylindrical wall 1b of the housing 1 for the needle 2 surrounds this latter wall up to the level where it reaches the base of the housing 1 delimited by the cylindrical wall 1b. A radial portion 1d of this wall extends outwards and terminates in a third cylindrical wall 1e, concentric with the other two but extending back to a higher level than they do and bounding an access opening 7 (FIG. 1b).

As FIG. 1a shows the overall shape of the illustrated container 1-1e for the needle 2 is that of a cylindrical stand whose base plate 1d is intended to provide a stable supporting surface when the tip 3 of the injection device 4 is being connected to the connecting end 2a of the hypodermic needle 2, In addition, the exterior cylindrical wall 1e has an internal diameter selected to match the external diameter of the body 5 of the injection instrument 4 so that it offers a guiding surface for that body when the tip 3 of the injection instrument 4 is being connected to the socket formed by the connecting end 2a of the needle 2. The ergonomic shape of the container 1-1e and the guiding surface make it possible to connect the instrument 4 to the needle 2 without holding the container and simply by placing it on a flat surface and applying sufficient pressure along the axis of the instrument 4 to deform a rib 2b located on the inner face of the socket 2a and allow it to engage with a groove or thread 3a located on the tip 3 of the injection instrument 4. The instrument 4 needs then merely to be withdrawn from the container as shown in FIG. 1b to be ready for the injection of the product contained in its cartridge 6.

In a preferred version of the invention several containers 1-1e are arranged side by side and linked to one another by a flat surface 1f forming a shared stand and extending as far as the upper ends of the exterior cylindrical walls 1e of the different containers 1-1e. This arrangement substantially enlarges the shared surface supporting the individual containers attached to one another, making it easier to grasp and thereby facilitating the operations involved in connecting the individual needles to the injection instrument 4.

Figure 2:
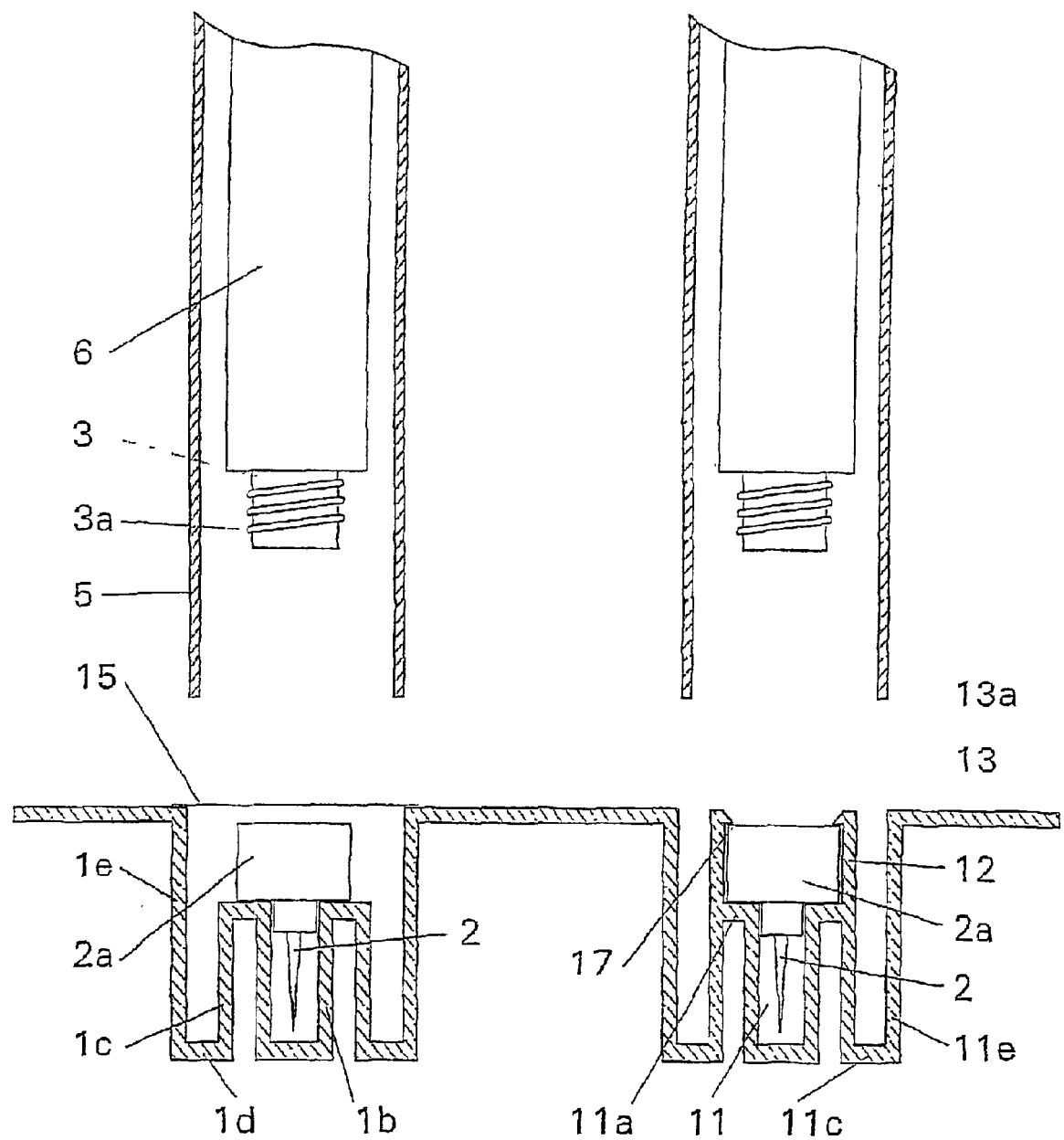
FIG. 2 is a vertical section of a first variation.

In a, still more advantageous version of the invention, illustrated in FIG. 2, the flat surface if linking the individual containers 1-1e can also serve to link to them the extractors of the needles 2 used to separate them from the injection instrument 4.

FIG. 2 shows part of an assembly of containers arranged side by side comprising two containers of which that marked 1-1e is identical with the container in FIGS. 1a, 1b. The other container serves as a needle extractor. Its overall aspect is similar to that of container 1-1e which is intended to contain a sterile needle 2. It also has a housing 11 for receiving a needle 2. This housing 11 is identical to the housing 1. Its upper end terminates in a lip 11a on which rests the outer face of the socket forming the connecting end 2a of the needle 2. In this extractor the second cylindrical wall 11c surrounding the wall bounding the housing 11 is continued upwards as far as the upper end of the exterior wall 11e by several elastic arms 12, forming between them a cylindrical receptor whose diameter matches that of the connecting end 2a of the hypodermic needle 2.

These elastic arms terminate in locking elements 13 projecting inwards into the receptacle formed between the elastic arms 12 and bounding an opening 17 of variable diameter. The length of the elastic arms 12 is selected so that the lower face of the locking elements 13 is located precisely at the level of the upper face of the connecting end 2a of the needle 2 when the lower face of this same end 2a is resting against the lip 11a. The upper face 13a of these locking elements is bevelled. This bevelled face 13a has the effect, when the used hypodermic needle 2 is moved against it, guided by the cylindrical surface 5 of the barrel of the injection instrument 4 which is guided by the inner face of the exterior cylindrical surface 11e of the extraction container 11-11e, and when pressure is exerted downwards along the axis, of creating a centrifugal radial component allowing the elastic arms 12 to be parted, thereby increasing the diameter of the opening 17 and making it possible to insert the connecting end 2a of the hypodermic needle 2 through the opening 17 into the receptacle formed between the arms 12.

The elastic arms 12 resume their initial position as soon as the lower face of the connecting end 2a of the needle 2 rests against the lip 11a of the housing 11. The lower face of the locking elements 13, engaged with the upper surface of the connecting end 2a, prevents the needle 2 from escaping from the container, in which it is now trapped. By exerting traction on the injection instrument 4 while holding on to the extraction container 11-11e it is possible to separate the injection instrument 4 from the hypodermic needle 2 which remains trapped.

Figure 3C:
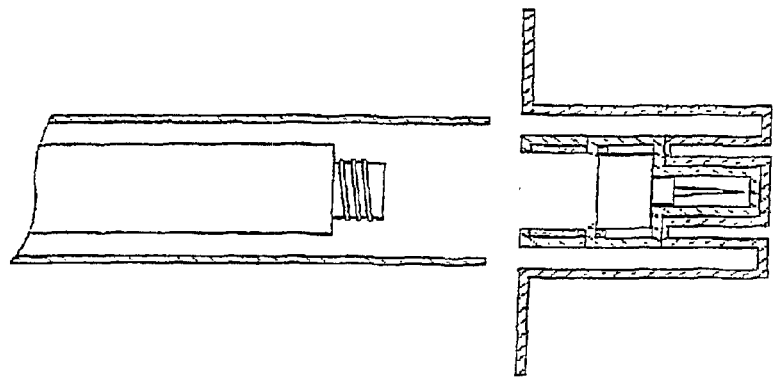
FIGS. 3a, 3b, 3c are vertical sections of a second variation, showing three successive stages in the use of a hypodermic needle.

In the variation described in connection with FIG. 2 two separate containers marked respectively 1-1e, 11-11e, are needed for each needle 2, one for the sterile needle 2 and the other for the needle 2 after use. We shall now describe, in connection with FIGS. 3a through 3c, a variation in which one single container can successively receive a sterile needle 2 and then be used to extract and stock the used needle 2.

In this variation there is a container 21-21e more or less identical to the preceding containers, with three cylindrical walls 21b, 21c, 21e, but in which the housing 21 formed by the cylindrical wall 21b, instead of receiving the hypodermic needle 2 directly, receives another receptacle 22 formed by two cylindrical coaxial parts, a lower one 22a, housed and fixed inside the wall 21b of the housing 21, and an upper one 22b, extending as far as the upper end of the exterior cylindrical surface 21e of the container 21-21e.

This differs from the preceding embodiments in that the upper part of the receptacle 22, installed above the housing 21 of the needle 2 properly so called, is of a height approximately twice that of the connecting end 2a of the hypodermic needle 2. Elastic arms 22c are located in the lower part of the upper cylindrical wall 22b of the receptacle 22. These elastic arms 22c are designed similarly to the elastic arms 12 in FIG. 2. They too terminate at their upper ends in locking elements 23, identical to the locking elements 13 in FIG. 2. These elastic arms 22c and the locking elements 23 play the same role as the corresponding parts in FIG. 2.

Figure 3B:
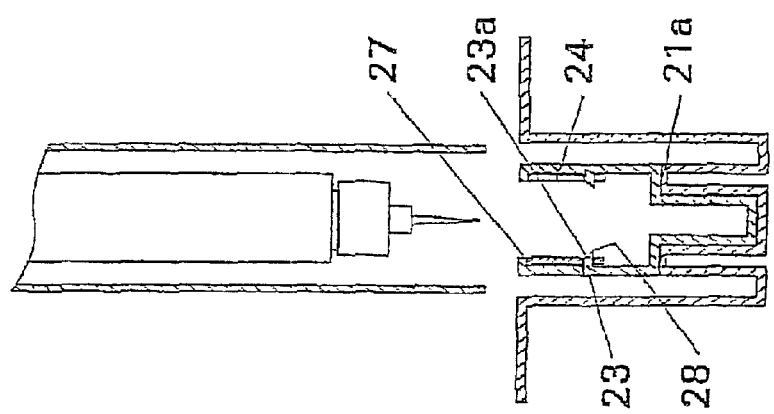
Figure 3A:
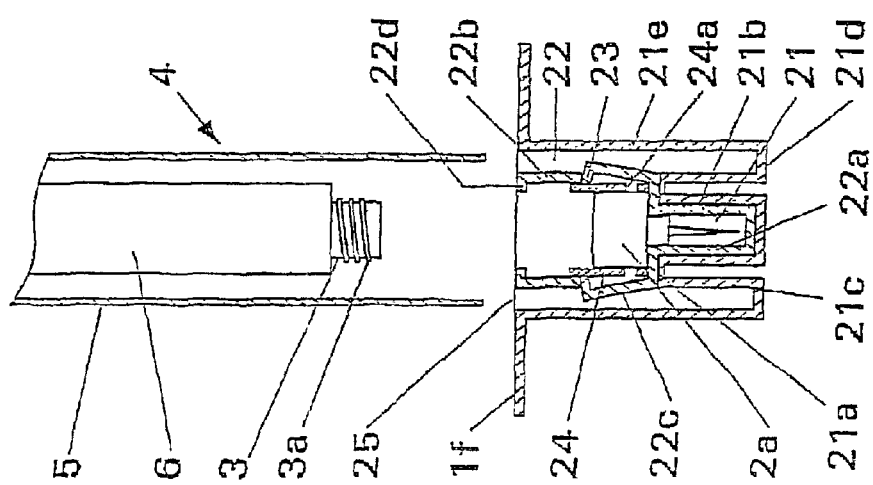

As is shown in FIG. 3a a ring 24, having passages 24a at its base, surrounds the connecting end 2a of the needle 2. The dimensions of this ring 24 permit it to project slightly beyond the upper surface of the connecting end 2a of the needle 2, so that the locking elements 23 and the elastic arms 22c are kept back, as is shown in FIG. 3a. The diameter of the ring 24 is selected so that it will be retained by friction around the connecting end 2a. A cap 25 which can be pierced closes the upper opening of the container 21-21e.

When the user wishes to connect the needle 2 enclosed in the container 21-21e to the tip 3 of the injection instrument 4 the lower rim of the cylindrical wall 5 of the barrel of the instrument 4 is centred on the cap 25 and then pressure is exerted on this instrument 4 along its axis. The first effect of this pressure is to pierce the cap 25. The instrument 4 is then guided by the cylindrical wall 21e of the container 21-21e, bringing the tip 3 of the instrument 4 into the cavity of the socket forming the connecting end 2a of the hypodermic needle 2. The connection between this needle 2 and the interior wall of this socket is effected in the manner described above with regard to the embodiment in FIG. 1a.

When the needle 2 connected to the tip 3 is withdrawn along its axis it draws with it the ring 24 until it rests against a lip 22d formed at the upper end of the cylindrical wall of the upper part 22b of the receptacle 22. The internal diameter of this lip 22d matches approximately that of the connecting end 2a of the needle 2, thus allowing this needle to be easily extracted from the container 21-21e by causing slippage between the connecting end 2a and the ring 24. Obviously, the frictional force between these two pieces must be less than the tractional force which must be exerted between the needle 2 and the injection instrument 4 for the needle 2 to be separated from the instrument.

As is shown in FIG. 3b, at the end of the movement of the ring 24 the passages 24a are opposite the locking elements 23, allowing the devices to pass through them because of the elasticity of the arms 22c which resume their initial shape and to project from the inner face of the ring 24.

As soon as the sterile needle has been removed from the container as described above the latter is ready to receive the used needle and to separate it from the injection instrument 4. As can be seen, this separation is effected in a manner identical to that described in connection with FIG. 2. The parts of the locking elements 23 which project within the ring 24 have oblique upper faces 23a, so that the axial pressure exerted upon these oblique faces when the connecting end 2a of the needle 2 is inserted will force them back allowing this connecting end to be pushed until it comes to rest against the lip 21a formed at the upper end of the housing 21 for the needle 2. At this moment the locking elements 23 are freed, so that they can close again above the upper face of the connecting end 2a of the needle 2, trapping the needle in the container 21-21e. The injection instrument 4 can then be separated by exerting axial traction on it while holding the container 21-21e whose ergonomic shape forms an interface making it easy to grasp, whereas this operation would be very difficult, in fact impossible, for an inexperienced user to perform if the container were not there. The advantage of the ergonomic interface is further increased when several containers are arranged side by side, linked by a shared horizontal wall if, which improves the purchase on the stand shared by these containers 21-21e.

In the variation illustrated in FIGS. 4a through 4c the container takes the form of a tubular body 31 bounding a cylindrical housing 36 accessed through an opening 38. The hypodermic needles 2 are inserted successively in the housing 36. In this variation the connecting socket 2a of the needle 2 serves also as a spacer keeping the needles separated along their axes. As this connecting socket 2a has to dilate radially when it is being connected to the tip 3 of the injection instrument 4 the external diameter of this connecting socket 2a is very slightly less than the internal diameter of the tubular body 31, so as to prevent the connection operation from causing the needle to become jammed in the tubular body 31 and thereby making it difficult to remove. There is another portion 2d, located between the connecting socket 2a and the needle 2, whose diameter matches the internal diameter of the tubular body 31, which serves to keep the needles within this body.

These needles 2 are accessible from one end of the tubular body 31 and connection with the zip 3 of the injection instrument is effected in the manner described above. In this example there are six needles lodged in the tubular body. The first needle 2, which will be the last to be used, is held in place by a supporting device 32 positioned by sliding it into the tubular body 31. The frictional force between this supporting device 31 and the interior wall of the tubular body 31 is however selected so that it will resist the pressure required to connect the needle 2 and the injection instrument 4. This supporting device 32 has two housings 32a, 32b positioned with mirror symmetry in relation to the centre of the device 32, with their ends facing outwards and open. The diameter of these housings is selected so that they can receive the intermediate portion 2c of the hypodermic needle.

This supporting device 32 and the axial housings 32a, 32b make it possible for the needles 2 withdrawn from the tubular body 31 to be inserted after use through the other end of the tubular body 31 and then separated from the injection instrument 4. For this purpose the other end has elastic arms 33 terminating in locking elements 34 like those in the embodiments described above. These locking elements 34 have bevelled outer faces 34a bounding an opening 37 of variable diameter. These bevelled, faces 34a are intended to convert the axial force exerted upon them by the portion 2d of the needle 2 into a radial component which makes it possible to bend the elastic arms 33 and thus increase the diameter of the opening 37 in order to allow the connecting end 2a to pass through. The supporting device 32 must therefore slide each time a used needle 2 is inserted through the end of the tubular body 31 provided with the locking elements 34.

As is shown in FIG. 4c the locking elements 34 become engaged in a space created between the end of the connecting socket 2a and the cartridge 6, so that traction exerted between the injection instrument 4 and the tubular body 31 makes it possible to separate the instrument 4 from the needle 2 which is trapped in the tubular body 31. The ergonomic shape of the latter offers a firm grip which makes it easy to perform this operation.

What is claimed is:

1. A storage container for a hypodermic needle, the hypodermic needle having a connecting end which has connectors complementary with connectors on the tip of an injection instrument, one of the connectors having radial elasticity and devices for converting an axial force exerted between the needle and the injection instrument into at least one radial component capable of deforming the elastic connectors, the container having a housing designed for holding the needle in a determined position, and an opening giving access to the housing;

wherein an exterior wall bounding the housing has a cylindrical guiding surface coaxial with the longitudinal axis of the housing and designed to engage with a complementary guiding surface of the instrument so that the engagement of these guiding surfaces with each other allows the complementary connectors to be put in the assembling position, following the exertion on the devices for converting an axial force into at least one radial component of a pressure coaxial with the longitudinal axis of the housing, wherein the housing holding the hypodermic needle in a determined position has two coaxial openings at a distance from each other, the first of these openings having a fixed diameter approximately equal to the diameter of the connecting end, while the second opening is delimited by elastically radial devices so as to allow its diameter to vary between the minimum diameter and the maximum diameter, and in that a ring having an internal diameter approximately equal to that of the first opening grips the connecting end while projecting from its rear face, thus keeping back the locking elements, this ring having, at a distance from its projecting end equal to the distance between the two said openings, passages whose dimensions allow the locking elements to pass through them and to project within the ring, so that, once the complementary connectors are connected together displacing the injection instrument outwards along its axis causes the hypodermic needle and the ring to shift until the ring rests against the rim of the first opening, in which position the locking elements pass through the passages and the ring separates from the connecting end, while the reinsertion of the connecting end into the housing causes this connecting end to be held in position by the locking elements.

2. A container according to claim 1, wherein the shape and dimensions of the exterior wall bounding the housing are selected to create, with the needle, an ergonomic positioning or handling interface, in order to facilitate the connection of the complementary connectors on the needle and on the tip, respectively.

3. A container according to claim 2, wherein a number of housings are arranged side by side on a shared stand.

4. A container according to claim 2, wherein the wall of the housing is of a tubular form and that in it a number of hypodermic needles are placed successively in equivalent positions so as to be accessible to the injection instrument from one end of the wall, while the other end has the radially elastic locking elements to allow its diameter to vary between a minimum diameter and a maximum diameter at least equal to the diameter of the connecting end and at least one piece associated with the locking elements for the purpose of converting an axial force exerted on the piece into at least one radial component which can be applied to the locking elements in order to deform them radially so as to increase the diameter of the opening.

5. A container according to claim 1, wherein the exterior wall has a flat surface extending perpendicularly to the axis of the hypodermic needle held in the determined position, the area of this surface being capable of imparting to the needle a stable vertical position when the flat surface is placed on a horizontal supporting surface.

6. A container according to claim 5, wherein a number of housings are arranged side by side on a shared stand.

7. A container according to claim 1, wherein the exterior wall bounding the housing has, in addition, devices for separating the connecting end of the hypodermic needle from the tip of the injection instrument, the container having an opening delimited by locking elements with radial elasticity allowing its diameter to vary between a minimum diameter and a maximum diameter at least equal to that of the connecting end and at least one device associated with the locking elements for converting an axial force exerted on the device into at least one radial component which can be applied to the locking elements to deform them radially so that the diameter of the opening is increased when the connecting end is displaced along its axis with its needle pointing forwards through the opening and the initial diameter is resumed after the connecting end has passed through and the locking elements are allowed to engage with the rear face of the connecting end, thereby allowing the connecting end to be separated from the tip by the application of tractional force along the axis of the instrument.

8. A container according to claim 7, wherein a number of housings are arranged side by side on a shared stand.

9. A container according to claim 7, wherein the opening delimited by the radially elastic locking elements serves as the access opening of a closed housing.

10. A container according to claim 1, wherein a number of housings are arranged side by side on a shared stand.

11. A container according to claim 1, wherein the access opening is closed by a cap which can be pierced.

* * * * *